United States Patent
Rump et al.

(10) Patent No.: US 10,975,079 B2
(45) Date of Patent: Apr. 13, 2021

(54) 4-AMINO-3-PHENYLAMINO-6-PHENYLPYRAZOLO[3,4-D]PYRIMIDINE DERIVATIVES FOR USE AS BCRP INHIBITORS IN THERAPEUTIC TREATMENTS

(71) Applicant: SCANDION ONCOLOGY A/S, Copenhagen (DK)

(72) Inventors: Steffen Rump, Hannover (DE); Henning Weigt, Isernhagen (DE)

(73) Assignee: Scandion Oncology A/S, Copenhagen (DK)

( * ) Notice: Subject to any disclaimer, the term of this patent is extended or adjusted under 35 U.S.C. 154(b) by 0 days.

(21) Appl. No.: 15/555,152

(22) PCT Filed: Feb. 24, 2016

(86) PCT No.: PCT/EP2016/053843
§ 371 (c)(1),
(2) Date: Sep. 1, 2017

(87) PCT Pub. No.: WO2016/139093
PCT Pub. Date: Sep. 9, 2016

(65) Prior Publication Data
US 2018/0044341 A1 Feb. 15, 2018

(30) Foreign Application Priority Data
Mar. 4, 2015 (EP) .................... 15157648

(51) Int. Cl.
| | | |
|---|---|---|
| A61K 31/15 | (2006.01) | |
| A61K 31/519 | (2006.01) | |
| A61K 31/565 | (2006.01) | |
| A61K 31/566 | (2006.01) | |
| A61K 31/5685 | (2006.01) | |
| A61K 45/06 | (2006.01) | |
| C07D 487/04 | (2006.01) | |
| A61K 31/015 | (2006.01) | |

(52) U.S. Cl.
CPC .......... *C07D 487/04* (2013.01); *A61K 31/015* (2013.01); *A61K 31/519* (2013.01); *A61K 31/565* (2013.01); *A61K 31/566* (2013.01); *A61K 31/5685* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 8,962,634 B2 | 2/2015 | Makarov et al. | |
| 9,790,225 B2 | 10/2017 | Wutzler et al. | |
| 2003/0165465 A1* | 9/2003 | Roberts | A61K 2300/00 424/93.2 |
| 2008/0057036 A1* | 3/2008 | Johansson | A61P 35/00 424/93.6 |
| 2008/0193479 A1* | 8/2008 | Au | A61K 35/768 424/204.1 |
| 2015/0001157 A1 | 1/2015 | Johnson | |

FOREIGN PATENT DOCUMENTS

| | | |
|---|---|---|
| BR | PI1104409 A2 | 8/2015 |
| CN | 105413094 A | 3/2016 |
| DE | 10 2011 116373 | 4/2013 |
| DE | 10 2012 004736 | 4/2013 |
| EP | 2049540 A1 | 4/2009 |
| JP | 2007-509728 | 4/2007 |

(Continued)

OTHER PUBLICATIONS

Sausville et al. (Cancer Research, 2006, vol. 66, pp. 3351-3354) (Year: 2006).*
Johnson et al. (British J. of Cancer, 2001, 84(10):1424-1431) (Year: 2001).*
Pan et al. Mol. Pharmaceutics 2013, 10, 4, 1236-1248 (Year: 2013).*
Wutzler et al (WO2013053942) translation (Year: 2013).*
Mao et al (The AAPS Journal, vol. 17, No. 1, Jan. 2015) (Year: 2015).*

(Continued)

*Primary Examiner* — Jared Barsky
(74) *Attorney, Agent, or Firm* — BakerHostetler

(57) ABSTRACT

The present invention relates to 5-amino-3-phenylamino-6-phenylpyrazolo[3,4-d]pyrimidine derivatives of the general formula (I) or pharmaceutically acceptable salts or propharmacons thereof for use as BCRP inhibitors, wherein at least one hydrogen atom in at least one of the phenyl groups A and B is substituted by a substituent $R^H$, which has a Hammett constant $\sigma_p$ greater than 0.23. For corresponding compounds, surprisingly a particularly high inhibitory activity against BCRP has been discovered which can be exploited for suppressing the multidrug resistance modulator BCRP, thus providing an improvement in efficacy of BCRP affected drugs. This has useful implications for cancer and HIV treatment.

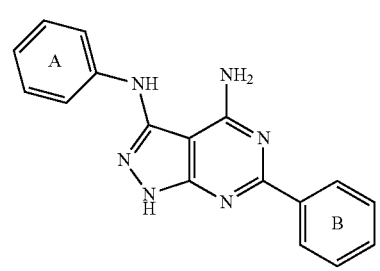

(I)

16 Claims, No Drawings

(56) References Cited

FOREIGN PATENT DOCUMENTS

| WO | 2000/043394 | | 7/2000 | |
|---|---|---|---|---|
| WO | 2005/044377 | | 5/2005 | |
| WO | 2007/147401 | A1 | 12/2007 | |
| WO | 20101127757 | A2 | 11/2010 | |
| WO | WO2013053942 | * | 4/2013 | ........... C07D 487/04 |

OTHER PUBLICATIONS

Mao et al., "Role the of the Breast Cancer Resistance Protein (BCRP/ABCG2) in Drug Transport—an Update," AAPS Journal vol. 17, No. 1 Jan. 2015.*

Robey et al., "Revisiting the role of ABC transporters in multidrug-resistant cancer", Nature Reviews, © 2018, 13 pages.

Toyoda et al., "Inhibitors of Human ABCG2: From Technical Background to Recent Updates With Clinical Implications", Frontiers in Pharmacology, Mar. 2019, vol. 10, Article 208, 1-9.

Wang et al., "Breast Cancer Resistance Protein (BCRP/ABCG$_2$) Induces Cellular Resistance to HIV-$_1$ Nucleoside Reverse Transcriptase Inhibitors", Molecular Pharmacology, Jan. 2003, 63(1), 65-72, Abstract.

Fan et al; Chemical reactivity probes for assessing abiotic natural attenuation by reducing iron minerals; Env. Scie & Tech; vol. 50; pp. 1868-1876; 2016.

Hui Li et al; Wheat straw biochar-supported nanoscale from ground water; PLOS ONE; pp. 1-10; 2017.

Kopinke et al; Reductive dechlronination in water: Interplay of sorption and reactivity; Appl. Catalysis B: Environmental; vol. 81; pp. 747-753; 2016.

Liu Jing et al; Effect of reactive bed mineralogy on aresnic retention and permeability of synthetic; col. 394, pp. 530-538; 2012.

Woojin et al; Abiotic Reductive Dechlorination of Chlorinated Ethylens by Iron-Bearing Soil Minerals; Env. Scie.&Tech; vol. 36, No. 24, pp. 5348-5354, 2002.

"Structure-activity relationships: quantitative approaches, The significance in drug design and mode-of-action studies", Kagaku no Ryoiki, Special Issue No. 122, Nankodo Co., Ltd., Jan. 10, 1979, 96-103 (Attached English Translation of Japanese Patent Application P2017-564796 Office Action, Notice of Reasons for Rejection, dated Dec. 10, 2019, noting citation of Non-Patent Literature Document—4 pages).

Boere, RT, et al., J. Organomet. Chem., 1987, 331, 161-167.

Dann O. et al., Synthesen biskationischer, trypanocider 1-Benzofuran—Verbindungen, Justus Liebigs Ann. Chem., 1982, 1836-1839.

Garigipati RS., Tetrahedron Lett., 1990, 31, 1969-1978.

Hansch et al., A survey of Hammett Substituent Constants and Resonance and Field Parameters, Chem. Rev., 1991, 97, 165-195.

Leonard et al., "Classical QSAR Modeling of HIV-1 Reverse Transcriptase Inhibitor 2-Amino-6-arylsufonylbenzonitriles and Congeners", QSAR & Combinatorial Science, 2004, 23(1), 23-35.

Paturi D.K. et al., Int. J. Pharm., 2010, 384, 32-38.

The International Transporter Consortium Membrane Transporter in Drug Development, Nat. Rev. Drug Disc., 2010, 9, 215-236.

Tominaga et al., J. Heterocycl. Chem., 1990, 27, 775-779.

Ambjorner, et al: MDPI, The Pyrazolo[3,4-d]pyrimidine Derivative, SCO-201, Reverses Multidrug Resistance Mediated by ABCG2/BCRP, Cells 2020, 9, 613 pp. 1-22.

Kapil et al., "4-Substituted-2-phenylquinazolines as inhibitors of BCRP", Bioorganic & Medicinal Chemistry Letters, vol. 22, No. 21,2012, pp. 6766-6769.

Krauze et al., "Thieno[2,3-b]ayridines—A new class of multidrug resistance (MOR) modulators", Bioorganic & Medicinal Chemistry, vol. 22, No. 21, Nov. 1, 2014, 5860-5870.

Leonard el al., "Comparative Classical QSAR Modeling of Anti-HIV Thiocarbamates", QSAR & Combinatorial Science, 2007, 26(9), 980-990.

Roy et al., "QSAR by LFER model of cytotoxicity data of anti-HIV 5-phenyl-1-phenylamino-1H-imidazole derivatives using principal component factor analysis and genetic function approximation", Bioorganic and Medicinal Chemistry, 2005, 13(8), 2967-2973.

Tsuno, "The Hammett Relationship", The Journal of the Society of Synthetic Organic Chemistry, Japan, 1965, 23(8), 631-642.

* cited by examiner

4-AMINO-3-PHENYLAMINO-6-PHENYLPYRAZOLO[3,4-D]PYRIMIDINE DERIVATIVES FOR USE AS BCRP INHIBITORS IN THERAPEUTIC TREATMENTS

CROSS-REFERENCE TO RELATED APPLICATIONS

This application is the National Stage of International Application No. PCT/EP2016/053843, filed Feb. 24, 2016, which claims the benefit of EP application number 15157648.5, filed Mar. 4, 2015, the disclosures of which are incorporated herein by reference in their entireties.

The invention concerns 4-amino-3-phenylamino-6-phenylpyrazolo[3,4-d]pyrimidine derivatives for use as BCRP inhibitors in therapeutic treatments and in particular for cancer and HIV therapy. The inventive BCRP inhibitors are especially effective when used in combination with a second pharmaceutically active agent, which itself is a potential substrate for BCRP.

BCRP transporter (Breast Cancer Resistance Protein), also referred to as ABCG2, plays an important role in the disposition and distribution of xenobiotics, similar to the transporter P-gp and MRP1 (Cf. R. W. Robey et al., Cancer Metastasis Rev. (2007) 26, S. 39-57). BCRP is an efflux transporter that prevents such substances from penetrating tissues such as the brain, gut, and tumors and is also involved in biliary excretion and to some extent, renal excretion.

The BCRP transporter is highly expressed in tissue barriers such as the colon, small intestine, blood-brain barrier (BBB), placenta and liver canalicular membrane, indicating a role in barrier function. In polarized cells of the gut, kidney and liver epithelium, BCRP is localized to the apical membrane where it mediates unidirectional transport of substrates to the luminal side of the organ acting as an efflux pump.

TABLE 1

Physiological role of BCRP in various tissues:

| Tissue | Physiological role |
|---|---|
| Placenta | fetus protection from toxins |
| Liver and biliary tract | hepato-biliary excretion, biliary excretion of drugs, xenobiotics or endogenous compound conjugates |
| Stem cells | Side Population-Phenotype and protection against hypoxia |
| Intestine | reduction of drug absorption |
| Brain | protection against xenobiotics |
| Breast | secretion of B vitamin required for fat metabolism |
| Kidney | renal excretion |

BCRP (ABCG2) is a cellular transporter that transports a variety of structurally different molecules with pharmaceutical activity out of cells, a mechanism comparable to the physiological activity. This includes but is not limited to cytotoxic agents like Mitoxantron, Camptothecine (Topotecan, Irinotecan, SN-38), Flavopiridol and Methotrexat.

The effects of BCRP (ABCG2) inhibition are particularly interesting for application in chemotherapy. First, inhibition of BCRP within cancer cells increases the intracellular concentration of the cytostatic drug and thereby enhances the drug activity, especially if the cancer cells show an increased expression of BCRP transporter proteins as a resistance mechanism. Second, the inhibition of BCRP in the gastrointestinal tract results in an increased bioavailability and absorption of orally applied drugs and thereby an increase in their concentration in the blood plasma. An increase in plasma concentration and/or higher local drug concentrations in malignant cells can be expected to allow for a decrease of the overall drug dosage requirements for therapy and thereby lead to a reduction of side effects.

An overlap in substrate specificity between BCRP and P-gp (e.g. for glyburide, imatinib, methotrexate, mitoxantrone and prazosin) increases the barrier function of the efflux transporters. While P-gp generally transports hydrophobic compounds, BCRP additionally transports hydrophilic conjugated organic anions, particularly sulfates, with a high affinity.

BCRP actively transports xenobiotics including anticancer drugs and restricts the uptake of substrates from the gut lumen and through the BBB. BCRP expression in cancer cells confers drug-resistance in leukemia and higher levels are reported in solid tumors from the digestive tract, endometrium, lung and melanoma, although, contrarily, expression is generally low in breast cancer tumors. There is significant association between BCRP expression and tumor response to chemotherapy and progression-free survival. BCRP is implicated in Mitoxantrone efflux in 70% of the patients studied, despite very low mRNA levels. The placenta has high BCRP expression and this is believed to protect the fetus. E.g. the antidiabetic drug Glyburide has limited fetal penetration due to efflux by BCRP. In ABCG2 deficient pregnant mice co-administered with Topotecan (substrate) and GF120918 (inhibitor), the fetal plasma contained twice the levels of Topotecan as the mothers. In the liver, BCRP plays a major role in the biliary excretion but a minor role in the intestinal transport of Troglitazone sulfate.

Multidrug resistance inhibitors or modulators of P-gp (ABCB1), MRP1 (ABCC1) and BCRP (ABCG2) are classified in three generations. Compounds already used clinically for other therapeutic applications belong to the first generation (like verapamil, cyclosporin A, and quinidine). They showed high toxicity when applied in doses required for multi drug resistance reversal. The intensive search for more specific and less toxic compounds led to the development of next generations of multi drug resistance inhibitors. The third generation of multi drug resistance modulators represent novel molecules composed of structural features preselected on structure-activity relationships and then submitted to pharmacological screening. In contrast to the second-generation MDR modulators, these inhibitors are not cytochrome P450 3A4 substrates, and do not significantly influence the pharmacokinetic profile of co-administered drugs. However, none of these inhibitors has reached the market yet.

It has been shown that BCRP (ABCG2) plays a vital role in development of multi drug resistance in different forms of cancer treatment. Thereby identification of modulators for BCRP mediated drug resistance is of great interest. Even though only a small number of specific compounds have been identified as BCRP inhibitors thus far.

In addition, no clinical trials have yet been initiated in which the effectiveness of a BCRP specific inhibitor was studied together with a cytostatic agent in tumor therapy. Until now, only a broad spectrum inhibitor has been investigated clinically (GF120918). Elacridar (GF120918), a dual P-gp/BCRP inhibitor has been investigated extensively in preclinical and clinical studies.

Regarding BCRP specific inhibitors, the mycotoxin Fumitremorgin C, isolated from *Aspergillus fumigatus*, was discovered as one of the first highly potent, specific inhibitors of BCRP.

However, its pronounced neurotoxicity limited its use in vivo. Using solid phase synthesis to create a library of Fumitremorgin C derivatives, compounds, Ko132 and Ko143 were identified that appeared to be highly active substances with low cytotoxicity compared to Fumitremorgin C.

Despite of these advances in technology, there remains a need for effective and specific BCRP inhibitors which exhibit low cyto- and neurotoxicity and preferably also do not affect the P-gp transporter.

Pyrazolo[3,4-d]pyrimidine derivatives have recently been discovered as potent therapeutic agents for the treatment of viral infections such as in particular picornavirus infections. E.g. EP 2 049 540 A discloses 4-amino-3-arylamino-6-arylpyrazolo[3,4-d]pyrimidine derivatives and their use as antiviral agents. In WO 2013/053942, which is a follow up to EP 2 049 540, a specific group of highly potent 4-amino-3-arylamino-6-arylpyrazolo[3,4-d]pyrimidine was identified, which exhibit high antiviral activity against a great variety of rhinoviruses and CVB3-isolates. There is no suggestion in these applications, however, that these compounds would have inhibitory activity on proteins in the body of healthy mammals.

The purpose of the invention is to identify BCRP inhibitors and in particular BCRP-inhibitors having a high specificity for BCRP so that the P-gp transporter is preferably not affected.

This purpose is met by specifically substituted 4-amino-3-phenylamino-6-phenylpyrazolo[3,4-d]pyrimidine derivatives of the general formula I, including their pharmaceutically tolerated salt compounds, for use as BCRP inhibitors,

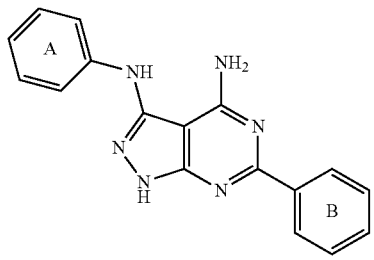

I wherein at least one hydrogen atom in at least one of the phenyl groups A and B is replaced by a substituent $R^H$, which has a Hammett constant $\sigma_p$ greater than 0.23, wherein every further hydrogen atom in each of the phenyl groups A and B can be replaced independently of each other by a residue $R^1$, wherein
- each $R^1$ independently can be a halogen, a saturated or unsaturated, linear or branched aliphatic radical with 1-7 chain members, a saturated or unsaturated, linear or branched alkanol radical with 1-8 chain members, $NO_2$, CN, $CONR^2_2$, $COR^2$, $COOR^2$, $OR^2$, $SR^2$, $NR^2_2$, $SO_2NR^2_2$, $CX_3$, $CR^2X_2$, $OCX_3$, $OCR^2X_2$, or phenyl;
- each $R^2$ independently is hydrogen, a saturated or unsaturated, halogenated or non-halogenated, linear or branched aliphatic radical with 1-7 chain members, benzyl, phenyl or naphtyl, a saturated or unsaturated, mono- or polyheterocycle with the heteroatoms N, S or O, wherein each of the above-mentioned groups can be independently substituted with fluorine, chlorine, bromine, trifluormethyl, alkyl, alkoxy, cyano, nitro, amino, aminoalkyl, C(O)-alkyl, C(O)O-alkyl, benzyl, phenyl or naphtyl; and
- X independently is F, Cl, Br, or I.

In the subclaims the advantage of specifically substituted 4-amino-3-phenylamino-6-phenylpyrazolo[3,4-d]pyrimidine derivatives are explained as well as more specific applications, without limiting the invention in any way.

4-amino-3-phenylamino-6-phenylpyrazolo[3,4-d]pyrimidine derivatives of the general formula I are advantageous, wherein at least one hydrogen atom in at least one of the phenyl groups A and B is replaced by a substituent $R^H$, selected from $NO_2$, CN, $CF_3$, $CCl_3$, $CBr_3$, $OCF_3$, $OCCl_3$, $OCBr_3$, $CHF_2$, $CHCl_2$, $CHBr_2$, $OCHCl_2$, CHO, COOH, COMe, COEt, COOMe or COOEt, preferably $CF_3$ or $OCF_3$.

It is an advantage that in one or both phenyl groups A and B one, two or three hydrogen atoms are replaced by a substituent $R^H$. In a special embodiment precisely one hydrogen atom in one of the phenyl groups A and B is replaced by a substituent $R^H$. The substituent $R^H$ can be in para position of the phenyl ring A or B.

In addition to $R^H$ each of the phenyl groups A and B can independently of each other carry further residues $R^1$. It is an advantage that the phenyl groups A and B independently of each other carry none, one, two or three further residues $R^1$, preferring none or a further residue $R^1$.

As alkyls it is worth considering in connection with the invention in particular linear or branched $C_{1-7}$-alkyls, for example, methyl, ethyl, n-propyl, i-propyl and butyl. The same applies to alkanols, alkylamines and alkylamides in connection with the invention.

The 4-amino-3-phenylamino-6-phenylpyrazolo[3,4-d]pyrimidine derivatives of the general formula I are preferably derivatives of the general formula II

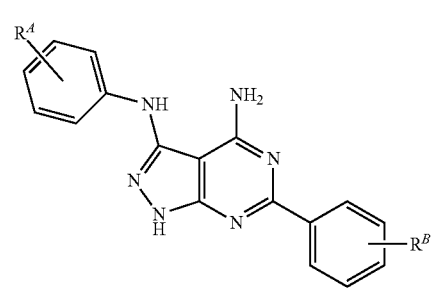

II wherein each substituent $R^A$, $R^B$ independently can be hydrogen, a halogen, a saturated or unsaturated, linear or branched aliphatic radical with 1-7 chain members, a saturated or unsaturated, linear or branched alkanol radical with 1-8 chain members, $NO_2$, CN, $CONR^2_2$, $COR^2$, $COOR^2$, $OR^2$, $SR^2$, $NR^2_2$, $SO_2NR^2_2$, $CX_3$, $CR^2X_2$, $OCX_3$, $OCR^2X_2$, or phenyl; and $R^2$ and X as defined above; wherein at least one of the substituents $R^A$, $R^B$ has a Hammett constant $\sigma_p$ greater than 0.23.

It is furthermore preferred that the 4-amino-3-phenylamino-6-phenylpyrazolo[3,4-d]pyrimidine derivatives fall within the scope of the general formula IIa

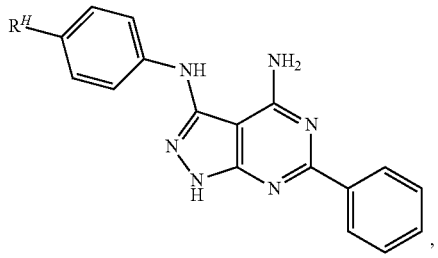

or IIb

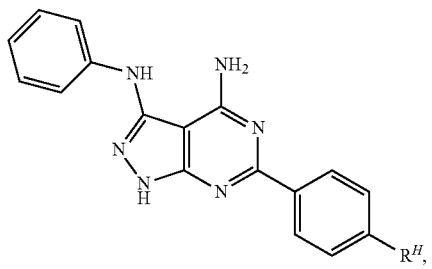

wherein $R^H$ is selected from $NO_2$, CN, $CF_3$, $CCl_3$, $CBr_3$, $OCF_3$, $OCCl_3$, $OCBr_3$, $CHF_2$, $CHCl_2$, $CHBr_2$, $OCHCl_2$, CHO, COOH, COMe, COEt, COOMe or COOEt, preferably $CF_3$ or $OCF_3$.

The use as a BCRP inhibitor is not subject to any relevant restrictions, except that it is a therapeutic use. In this context, the term therapeutic includes prophylactic uses. As preferred therapeutic uses the treatment of cancer and viral infections such as HIV can be mentioned.

Since the effectiveness of the inventive BCRP inhibitors primarily relies on the suppression of BCRP-activity, which inhibits the transport of active substances out of the cell, the use of the inventive BCRP inhibitors is most effective in combination with a second pharmaceutically active agent, which in the absence of the BCRP inhibitors would be available in the cell only at lower quantities. It is therefore preferred that the inventive BCRP inhibitor is used in combination with a second pharmaceutically active agent, which itself is a potential substrate for BCRP.

Whether a given compound represents a substrate for BCRP can be determined based on the efflux ratio of the compound in an assay with Caco-2 cells, wherein the efflux ratio is determined both in the presence and absence of 10 µM fumitremorgin C (FTC) (cf. e.g. The International Transporter Consortium (2010) Membrane transporters in drug development. *Nat Rev Drug Disc* 9; p. 215-236). This assay uses bidirectional transport studies from the apical to the basolateral side and vice-versa. The Caco-2 cell line is a commonly used in vitro model for identifying BCRP substrates. The cells are seeded on a Multiscreen™ plate (Millipore, Mass., USA) and form a confluent monolayer over 20 days prior to the experiment. The test substance is then added to either the apical or basolateral side of a confluent monolayer of the cells and the permeability is measured by monitoring its appearance on the opposite side of the membrane using LC-MS/MS after 120 Min.

The permeability coefficient ($P_{app}$) is calculated from the following equation:

$$P_{app} = \left(\frac{dQ/dt}{C_0 x A}\right)$$

where $dQ/dt$ is the rate of permeation of the drug across the cells, $C_0$ is the donor compartment concentration at time zero and A is the area of the cell monolayer.

The efflux ratio is calculated from the mean apical to basolateral (A-B) $P_{app}$ data and basolateral to apical (B-A) $P_{app}$ data.

$$\text{Efflux Ratio} = \left(\frac{P_{app}(B-A)}{P_{app}(A-B)}\right)$$

The permeability is assessed in the presence and absence of FTC (BCRP inhibitor) to confirm that the test substance is a substrate of BCRP. A test substance is considered a substrate for BCRP, if the net efflux ratio is ≥2 and the efflux is significantly inhibited by fumitremorgin C (i.e. inhibited to 50% or less of the efflux ratio without FTC).

In a preferred embodiment, the second pharmaceutical active agent in the above test shows a difference in the efflux ratio between the no-FTC containing and the FTC containing samples of 5 or more, in particular 10 or more and most preferably 20 or more. Typical BCRP-substrates include, but are not limited to cytostatic agents such as cytostatic anthrachinones (e.g. Mitoxantrone, Bisantrene, Aza-anthrapyrazole), cytostatic anthracyclines (e.g. Daunorubici, Doxorubicin, Epirubicin, Flavopiridol or Mitoxantrone), cytostatic antimetabolites (e.g. Methotrexate), cytostatic campothecins (e.g. 9-Aminocamptothecin (Rubitecan), Homocamptothecin, Irinotecan, SN-38 (active metabolite of Irinotecan), SN-38-glukuronide, Topotecan or Diflomotecan) and cytostatic Epipodophyllotoxins (e.g. Etoposide or Teniposide). Other BCRP substrates include antibiotics such as Ciprofloxacin, Ofloxacin, Norfoxcacin, Erythromycin and Nitrofurantoin, Calcium channel inhibitors such as Dipyridamole, Nifedipine and Nitrendipine, Glucuronide- and Sulfate-conjugates such as Benzo[a]pyrene-3-sulfate, Benzo[a]pyrene-3-glukuronide, Estrone-3-sulfate, Dehydroepiandrosterone sulphate and 17β-Estradiolsulfate, HMG-CoA reductase inhibitors such as Rosuvastatin, Pitavastatin and Cerivastatin, Porphyrins such as Heme, Pheophorbide A, Pyropheophorbide A-Methylester, Protoporphyrin IX, Phytoporphyrin, antiviral drugs, in particular nucleoside reverse transcriptase inhibitors such as Zidovudine, Lamivudine, Abacavir and combinations thereof, and substances such as Cimetidine, Folic acid, Methotrexate, Riboflavin, Sulfasalazine, Pantoprazole, Imatinib mesylate (STI571), Indocarbazole and Prazosin. Particularly preferred second pharmaceutically active agents are Topotecan and Trizivir, which is a combination of Abacavir, Lamivudine and Zidovudine.

Another possible application of the inhibitory properties of 4-amino-3-phenyl-6-phenylpyrazolo [3,4-d]pyrimidine derivatives mentioned above is the implementation of the compounds in a method to test the BCRP transporter activity. The present application thus also encompasses the use 4-amino-3-phenyl-6-phenylpyrazolo [3,4-d]pyrimidine derivatives as described above in a method for assessing the activity of a BCRP-transporter.

Also included are pharmaceutical compositions, which contain a 4-Amino-3-phenylamino-6-phenylpyrazolo[3,4-d]pyrimidine derivative according to the general formulas I, II, IIa or IIb. Such pharmaceutical compositions can contain further substances, for example, pharmaceutically acceptable excipients and carriers. In a particular aspect the pharmaceutical compositions include additional active ingredients such as those listed in the above paragraph as potential substrates for BCRP. In particular, it is preferred if pharmaceutical compositions is a combination of a 4-Amino-3-phenylamino-6-phenylpyrazolo[3,4-d]pyrimidine derivative as mentioned above and one or more of cytostatic agents, antibiotic agents, Calcium Channel inhibitors, glucuronide- and sulphate-conjugates, in particular of Benzo(a)pyrene, Estrone, Dehydroepiandrosterone and Estradiol, HMG-CoA reductase inhibitors, porphyrins and/or antiviral drugs, in particular nucleoside reverse transcriptase inhibitors. From among theses additions active agents the cytostatic agents as well as the antiviral drugs, in particular in the form of nucleoside reverse transcriptase inhibitors are especially preferred.

Surprisingly, it was found that the above described compounds are suitable for use in the co-treatment of conditions where the specific drug is transported out of the target cell via the BCRP transporter molecule. This has particular relevance for chemotherapy to overcome BCRP mediated drug resistance and to enhance the bioavailability and efficacy of the specific drug. Additionally, the BCRP specificity of the inventive compounds provide benefits to the safety and tolerability of co-medication in cancer therapy compared to the application of broad spectrum inhibitors (P-gp/MRP1/BCRP or P-gp/BCRP broad spectrum inhibitors. The BCRP specific inhibition of the inventive compounds, which does not affect the P-gp transporter, is beneficial to the potential drug-drug interaction profile of co-medication compared to broad spectrum inhibitors.

In addition, for some of the inventive compounds it has also been shown by in vitro DMPK analysis that the investigated compounds did not exhibit induction of inhibition of CYP 450 proteins—especially not of CYP3A4—so that they can be expected to have use as a $3^{rd}$ generation multi drug resistance modulator.

For these reasons, the pharmaceutical preparations which contain a compound of the formulas I, II, IIa or IIb, are particularly suitable for the treatment of cancer and viral infections such as HIV infections in particular.

The 4-amino-3-phenylamino-6-phenylpyrazolo[3,4-d]pyrimidine derivatives are characterised by the fact that they carry at least one substituent $R^H$ on one or on both phenyl groups, which has a Hammett constant $\sigma_p$ greater than 0.23. This value 0.23 corresponds to the Hammett constant $\sigma_p$ of the bromine, which shows the highest Hammett constant for the para position among the halogens.

The determination of the Hammett constants for different substituents is based on the ionization constants of the benzoic acid according to the Hammett equation $$\sigma_x = \log K_X - \log K_H$$

wherein $K_H$ is the ionization constant for benzoic acid in water at 25° C. and $K_X$ is the corresponding constant for a meta or para substituted benzoic acid. A method to determine the Hammett constant for different substituents in meta ($\sigma_m$) and para position ($\sigma_p$) as well as values already ascertained of a variety of substituents can be taken from the publication of Hansch et al., "A Survey of Hammett Substituent Constants and Resonance and Field Parameters", in Chem. Rev. 1991. 97, 165-195, which is incorporated herein in its entirety by reference. Of significance to this invention is thus exclusively the value a respectively for the para position ($\sigma_p$), irrespective of the position where at least one substituent $R^H$ is finally located.

Examples of the invention are compounds in Table 2, including their pharmaceutically tolerated salt compounds.

TABLE 2

| Compound | Formula | Solvent for crystallisation | Melting point ° C. | Molecular formula | MS EI (m/z) (M⁺) | Analysis Calculated (B) % Found (G) % | ¹H NMR (DMSO-d₆) δ, ppm |
|---|---|---|---|---|---|---|---|
| OBR-5-340 | 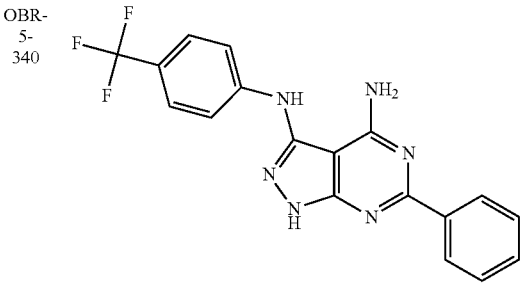 | THF, Toluene | — | $C_{18}H_{13}F_3N_6$ | 370.3312 | B; C 58.3; H 3.54; N 22.69 | — |

TABLE 2-continued

| Compound | Formula | Solvent for crystallisation | Melting point ° C. | Molecular formula | MS EI (m/z) (M+) | Analysis Calculated (B) % Found (G) % | ¹H NMR (DMSO-d₆) δ, ppm |
|---|---|---|---|---|---|---|---|
| MS-112 | (structure shown) | EtOH | — | $C_{18}H_{13}F_3N_6O$ | 386.3306 | B; C 55.96; H 3.39; N 21.75 | — |

The compounds indicated above for the referenced uses can be prepared via synthesising methods which will be briefly described in the following:

The below general diagram shows the synthesis of pyrazolo[3,4-d]pyrimidine 1 and includes in the first step the condensation of [bis(methylthio)methylen]malononitril 2 with phenylamines 3 in alcohol to phenyl derivatives 4. The latter can be isolated respectively and purified for further reactions or used directly without purification for subsequent reactions ("one-pot" reaction). The subsequent step constitutes the interaction of the phenyl derivative 4 with hydrazine or hydrazine derivatives. The reaction takes place by boiling for 1 to 4 hours and leads to a high yield of pyrazol 5. The final step of the synthesis of pyrazolo [3,4-d]pyrimidine 1 is the condensation of the pyrazol 5 with phenylamidine 6 in the presence of acetic acid, trifluoroacetic acid or sodium acetate.

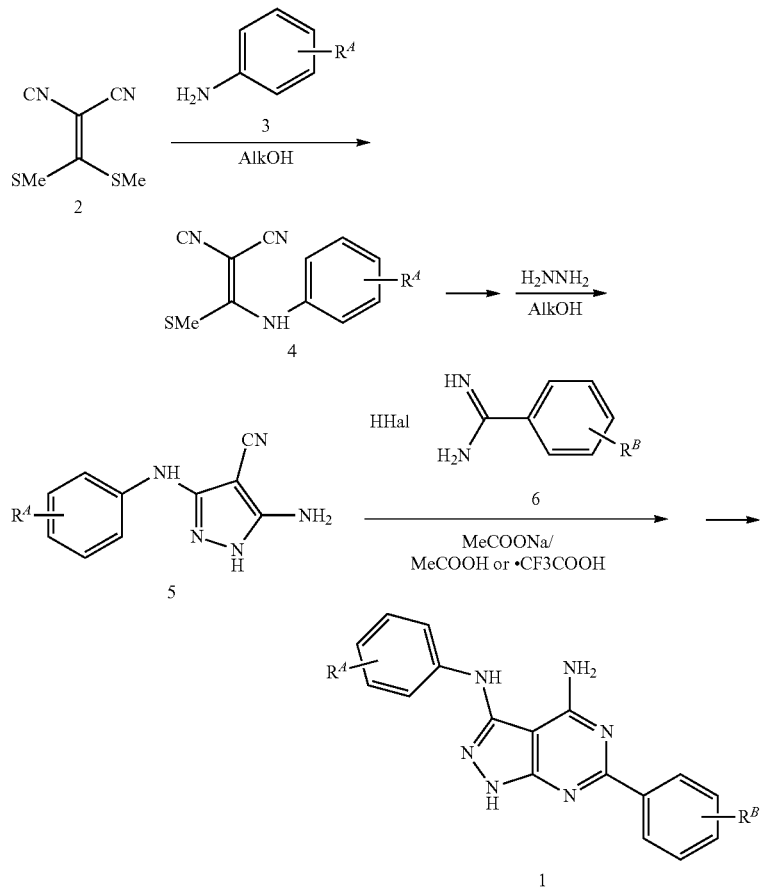

The compounds can be thereby obtained advantageously by transforming the pyrazol (5) in the last synthesis step with corresponding benzamidine hydrochloride in the presence of an excess of sodium acetate at 200-220° C. in the absence of solvents.

Alternatively the compounds can be obtained by converting the pyrazol (5) in the last synthesis step with corresponding benzonitrile (a large surplus) with microwave irradiation and in the presence of potassium-tert-butylate.

An alternative synthesis method is the "one-pot" reaction of malononitrile with aryl isothiocyanates in the presence of sodium hydride and a subsequent treatment of the reaction mixture with methyl iodide or dimethyl sulphate. In the process large amounts of enamine are produced. Here too the condensation of pyrazol 5 with arylamidines 6 in the presence of acid, such as acetic acid or trifluoroacetic acid, or their salts (acetate) is again the final synthesis step to produce pyrazolo[3,4-d]pyrimidine 1.

It has been shown that the conversion of the pyrazol (5) to pyrazolo[3,4-d]pyrimidine with particularly high yields can be done by using the benzamidine components as a free base and the reaction is carried out in polar solvents. An advantage of this method is also that the proportion of by-products which are difficult to separate can be minimised. This reaction can be effected, based on substituted 5-amino-4-cyano-3-phenylamino-pyrazoles (5) with optional substituted benzamidines as a free base (6) to 4-amino-3-(phenylamino)-6-phenylpyrazolo[3,4-d]pyrimidine (1) according to the following reaction diagram.

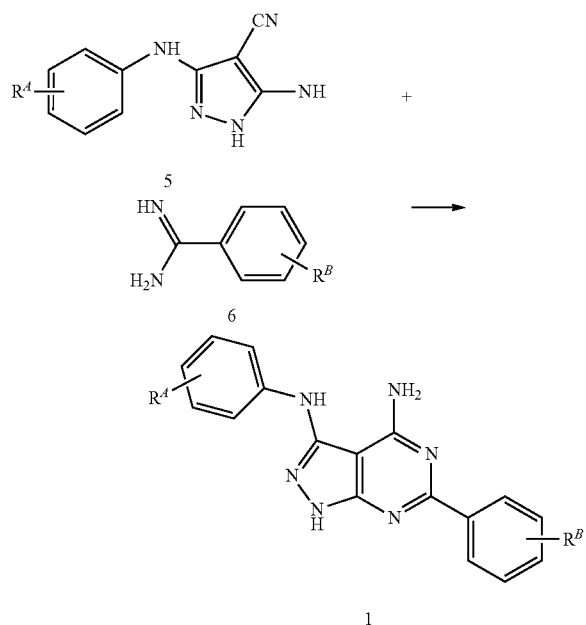

The residues $R^A$ and $R^B$ are substituents, as defined above for $R^1$.

Whilst the conversion described above is particularly suitable for the manufacture of 4-amino-3-phenylamino-6-phenylpyrazolo[3,4-d]pyrimidine derivatives of the above general formula (I), wherein at least one hydrogen atom in at least one of the phenyl groups A and B is replaced by a substituent $R^H$, which has a Hammett constant $\sigma_p > 0.23$, the method can also be used for the manufacture of 4-amino-3-phenylamino-6-phenylpyrazolo[3,4-d]pyrimidines, which have no such substituents, i.e. in which this residue represents hydrogen or a residue $R^1$, as defined above in connection with formula I.

The reaction shown in the above reaction diagram is effected in inert, polar organic solvents. Inert polar organic solvents are, for example, ether such as diethylether, methyl-tert.-butylether, 1,2-dimethoxyethane, glycol diethyl ether or diethylene glycol dimethyl ether, cyclic ether, such as dioxane, tetrahydrofuran, hydrocarbons, such as ethyl benzene, xylene, toluene or alcohols, such as ethanol, propanol, butanol, isobutanol and isopropanol. Particularly pure products are obtained by using n-butanol as a solvent. n-butanol should be used in a molar ratio of 1 to 10, in particular preferably 1.5 to 3, in relation to the initial value of the pyrazole derivative.

Within the scope of the present invention it emerged as particularly useful if the benzamidine (6) is freshly prepared in basic form (as free base). The synthesis is affected using the usual methods from the correspondingly available salt. It is best to use benzamidine (6) in a molar ratio of 1 to 1.5, based on the pyrazole derivatives (5).

The reaction is carried out at a temperature from 60 to 110° C., preferably 85 to 95° C., over 10-30 hours, preferably 18-20 hours.

The amino-3-(phenylamino)-6-phenylpyrazolo[3,4-d]pyrimidine (1) obtained in this way is cleaned by recrystallization. For this preferably tetrahydrofuran or a mixture of tetrahydrofuran with water or an organic solvent is used, in particular preferably with toluene. Alternatively to that the amino-3-(phenylamino)-6-phenylpyrazolo[3,4-d]pyrimidine can also be cleaned by precipitation from a hot solution in tetrahydrofuran with water or an organic solvent, preferably with toluene.

In the following examples special compounds of the general formula (I) are listed, which are suitable preferably for use in the treatment of cancer and virus infections such as HIV. These compounds can be prepared in a solution or a suspension in a pharmaceutically acceptable aqueous, organic or aqueous-organic medium for the local or parenteral application by intravenous, subcutaneous or intramuscular injection or for intranasal administration, or developed in the form of a tablet, capsule or aqueous suspension with a conventional carrier for oral administration or as a suppository.

The compounds presented in the formula (I) can thus be used in doses of 0.1 to 1000 mg/kg body weight.

Manufacture and Analysis of the 4-amino-3-phenylamino-6-phenylpyrazolo[3,4-d]pyrimidine Derivatives The structural clarification of the compounds of the invention is effected by the type of synthesis, elementary analyses, NMR spectroscopy and mass spectrometry.

Source Materials:

The 5-amino-4-cyano-3-phenylaminopyrazoles were synthesised according to the description of Tominaga Y et al. (J. Heterocycl. Chem., 1990, 27, 775-779). Arylamidines are synthesised according to the known prior art from the corresponding cyanogen source compounds (Boere, R T et al.: J. Organomet. Chem., 1987, 331, 161-167; Garigipati R S: Tetrahedron Lett., 1990, 31, 1969-1978; Dann O et al.: Justus Liebigs Ann. Chem., 1982, 1836-1839).

EXAMPLE 1

4-amino-3-(4-trifluormethyl-phenyl)amino-6-phenylpyrazolo[3,4-d]pyrimidine (OBR-5-340)

(6-phenyl-3-N-[4-(trifluormethyl)phenyl]-2H-pyrazolo[3,4-d]pyrimidine-3,4-diamine)

3.0 g (17.24 mmol) benzamidine hydrochloride hydrate and 2.2 g (23.0 mmol) sodium acetate are added to 2.3 g (11.5 mmol) 5-amino-4-cyano-3-(4-trifluormethylphenyl) aminopyrazol whilst stirring. The reaction mixture is heated for 30 min at 220° C. The resulting material is treated with 50 ml water, filtered and washed with 20 ml cold methanol and 20 ml cold ester. The product is cleaned by means of crystallisation from DMF/water.

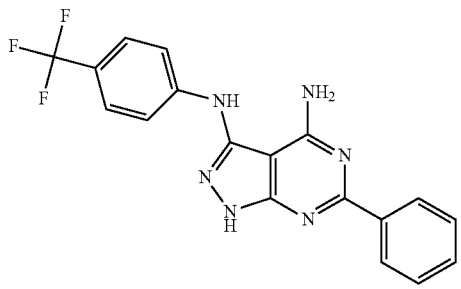 [SMILES: Nc1nc(-c2ccccc2)nc2[nH]nc(Nc3ccc(C(F)(F)F)cc3)c12]

OBR-5-340

EXAMPLE 2

4-amino-3-phenylamino-6-[4-(trifluormethoxy)-phenyl]pyrazolo[3,4-d]pyrimidine (MS-112)

(3-N-phenyl-6-[4-(trifluormethoxy)phenyl]-2H-pyrazolo[3,4-d]pyrimidine-3,4-diamine)

The manufacture was accomplished as described in example 1 using the correspondingly substituted precursor compounds.

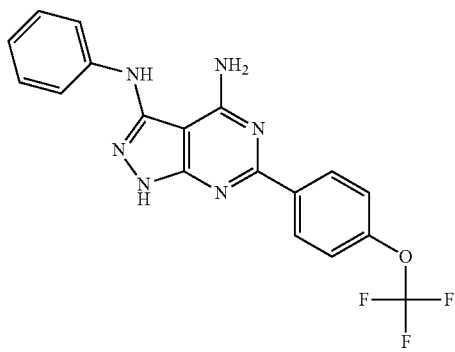 [SMILES: Nc1nc(-c2ccc(OC(F)(F)F)cc2)nc2[nH]nc(Nc3ccccc3)c12]

MS-112

ADME-Tox Studies on In Vitro Absorption of OBR 5-340 and MS 112

The IC-50 value of OBR 5-340 and MS 112 were determined according to the method described by Paturi D. K, et al in Int. J. Pharm. (2010), 384: 32-38. The source used for the determination was human recombinant CHO-K1 cells, while Hoechst 33342 (5 μm) was used as the substrate. The cells were incubated for 20 min at 37° C. and the detection was accomplished by fluorimetry.

Fluorimetric Inhibition Assay:

The percent of control is calculated using the following equation.

$$\text{Control}(\%) = \frac{\text{Compound} - \text{Background}}{T1 - \text{Background}} * 100$$

In this formula, "Compound" is the individual reading in the presence of the test compound. "T1" is the mean reading in the absence of the test compound. Background is the mean reading in the presence of the highest effective concentration of the reference inhibitor.

The percent of inhibition is calculated by subtracting the percent of control from 100. The IC50 value (concentration causing a half-maximal inhibition of the control value) is determined by non-linear regression analysis of the concentration-response curve using the Hill equation.

The results of the IC50 measurements are provided in the following table 3

TABLE 3

| Compound | IC50 |
|---|---|
| OBR-5-340 | 1.7 μM |
| MS-112 | ~100 μM |

Similar investigations on the inhibitory effect of the compounds OBR-5-340 and MS-112 on the P-pg transporter did not show any binding (the concentration response curves showed less than 25% effect at the highest validated testing concentration).

In a further test set it was evaluated by DPMK studies whether OBR-5-340 might exhibit unfavourable interactions with cytochrome P450. In these investigations it could be demonstrated that OBR-5-340 does not does not inhibit CYP1A, CYP2B6, CYP2C8, CYP2C9, CYP2C19, CYP2D6, and CYP3A. Also no induction of CYP1A2, CYP2B6, and CYP3A4 could be found. This data implies that OBR-5-340 does not significantly influence the pharmacokinetic profile of co-administered drugs. Based on these results, OBR-5-340 could be described as a highly potent third generation multidrug resistance inhibitor of BCRP.

The invention claimed is:

1. A method for increasing the efficacy of a pharmaceutically active agent for the treatment of cancer in a patient in need thereof comprising:
    administering the pharmaceutically active agent to the patient; and
    administering to the patient an amount of a compound of formula

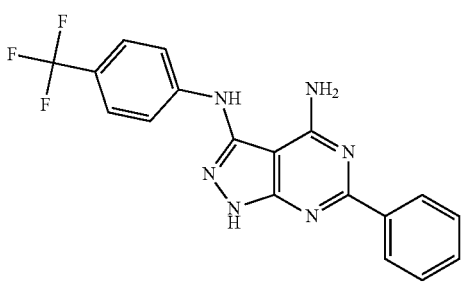

OBR-5-340 or a pharmaceutically acceptable salt thereof;
wherein the pharmaceutically active agent is a BCRP substrate; and
wherein the amount of the compound is effective in increasing the efficacy of the pharmaceutically active agent, as compared to the efficacy of the pharmaceutically active agent administered without the administration of the compound.

2. The method according to claim 1, wherein amount of the compound inhibits BCRP transporter activity in the patient.

3. The method of claim 1, wherein the pharmaceutically active agent exhibits a net efflux ratio of ≥2.

4. The method of claim 1, wherein the pharmaceutically active agent exhibits a net efflux ratio of 5 or more.

5. The method of claim 1, wherein the pharmaceutically active agent exhibits a net efflux ratio of 10 or more.

6. The method of claim 1, wherein the pharmaceutically active agent exhibits a net efflux ratio of 20 or more.

7. The method of claim 1, wherein the pharmaceutically active agent is a chemotherapeutic agent.

8. The method of claim 1, wherein the pharmaceutically active agent is a cytotoxic agent.

9. The method of claim 1, wherein the pharmaceutically active agent is a cytostatic agent.

10. The method of claim 1, wherein the pharmaceutically active agent is a cytostatic anthrachinone, a cytostatic anthracycline, a cytostatic antimetabolite, a cytostatic campothecin, or a cytostatic Epipodophyllotoxin.

11. The method of claim 10, wherein the cytostatic anthrachinone is mitoxantrone, Bisantrene, or Aza-anthrapyrazole.

12. The method of claim 10, wherein the cytostatic anthracycline is Daunorubici, Doxorubicin, Epirubicin, Flavopiridol or Mitoxantrone.

13. The method of claim 10, wherein the cytostatic antimetabolite is methotrexate.

14. The method of claim 10, wherein the cytostatic campothecin is 9-aminocamptothecin, Homocamptothecin, Irinotecan, SN-38, SN-38-glukuronide, Topotecan, or Diflomotecan.

15. The method of claim 10, wherein the cytostatic epopdophyllotoxin is etoposide or teniposide.

16. The method of claim 1, wherein the pharmaceutically active agent is Irinotecan.

* * * * *